US007339670B2

(12) United States Patent
Carrig et al.

(10) Patent No.: US 7,339,670 B2
(45) Date of Patent: Mar. 4, 2008

(54) WAVELENGTH NORMALIZED DEPOLARIZATION RATIO LIDAR

(75) Inventors: Timothy J. Carrig, Lafayette, CO (US); Christian Grund, Boulder, CO (US); John Marquardt, Berthoud, CO (US)

(73) Assignee: Lockheed Martin Coherent Technologies, Inc., Louisville, CO (US)

( * ) Notice: Subject to any disclaimer, the term of this patent is extended or adjusted under 35 U.S.C. 154(b) by 24 days.

(21) Appl. No.: 11/192,567

(22) Filed: Jul. 29, 2005

(65) Prior Publication Data

US 2007/0024849 A1 Feb. 1, 2007

(51) Int. Cl.
*G01N 21/00* (2006.01)

(52) U.S. Cl. ....................................... 356/337; 356/342

(58) Field of Classification Search ................ 356/436, 356/438, 441, 442, 337, 342
See application file for complete search history.

(56) References Cited

U.S. PATENT DOCUMENTS 6,639,674 B2 * 10/2003 Sokolov et al. ............. 356/369

OTHER PUBLICATIONS

J.H. Marquardt et al., "Measurement Of Bio-Aerosols With A Polarization-Sensitive, Coherent Doppler Lidar", 5th Joint Conference On Standoff Detection For Chemical And Biological Defense, Williamsburg, VA Sep. 24-28, 2001.
Theriault et al., "Passive Standoff Detection Of BG Aerosol: Method And Filed Trial Results", Process of SPIE, p. 163, vol. 5268, 2004.
Hecht, Wesley, Optics, 1998, 3rd ed., pp. 67, 340-342.
Grant, "Lidar For Atmospheric And Hydrospheric Studies", Tunable Laser Applications, F.J. Duarte ed., Marcel Dekker 1995.

Gurton, Ligon et al., "Measured Infrared Spectral Extinction For Aerosolized *Baccillus subtilis* var. Niger Endospores From 4 to 13 um", Applied Optics, 40(25), 2001.

Zakel et al., "High-Brightness Rapidly-Tunable Cr:AnSe Laser", 20th Anniversary Meeting Advanced Solid-State Photonics, Feb. 6-9, 2005, Vienna.

* cited by examiner

*Primary Examiner*—Roy M. Punnoose
(74) *Attorney, Agent, or Firm*—McDermott Will & Emery LLP

(57) ABSTRACT

A remote sensing optical system and method is disclosed that permits detection and discrimination of aerosols. The system outputs a plurality of wavelengths and is equipped with a polarization sensitive receiver capable of measuring the scattered energy in two orthogonal polarization states. By normalizing the depolarization to the total energy received and calculating the ratio of normalized depolarization at different wavelengths it is possible to use this ratio to discriminate materials having wavelength dependent depolarization properties. One use is the discrimination of bioaerosols such as anthrax from other airborne particular matter.

32 Claims, 4 Drawing Sheets

WAVELENGTH NORMALIZED DEPOLARIZATION RATIO LIDAR

GOVERNMENT LICENSE RIGHTS

The U.S. Government has a paid-up license in this invention and the right in limited circumstances to require the patent owner to license others on reasonable terms as provided for by the terms of contract F33615-01-C-6019 awarded by the Air Force Research Laboratory/MLKH.

BACKGROUND OF THE INVENTION

1. Field of the Invention

This invention is in the field of laser radar devices and, more specifically, to systems and methods remotely detecting the presence of species distributed in the atmosphere, such as biological species.

2. Relevant Background

Light Detection and Ranging (lidar) systems are used in numerous areas of practical interest to make remote measurements. In lidar systems a light beam is sent to a target and a detection system is used to extract information about the target. In some cases the target is classified as a "hard-target" and may consist of a material having properties or a location that one desires to determine. In other cases targets are distributed, meaning generally that they are not localized in space. Examples of distributed targets include particles suspended in the atmosphere, or aerosols, such as water droplets, sea salt, spores, pollen and dust; chemical plumes such as pipeline natural gas leaks and paint fumes; and background atmospheric gases such as ozone, water vapor and carbon dioxide.

Heightened concerns in recent years about potential use of airborne chemical and biological agents to cause harm has increased the urgency of finding methods to remotely detect and locate such agents. It has generally been found difficult to use remote sensing methods to a) detect threat species and b) reliably discriminate the threat species from other species that may also be present. In the case of biological agents like anthrax it is in principle possible to detect their presence by simply collecting scattered light from the particles. However, simple light scattering measurements often cannot tell the difference between types of aerosols, so the scattered light "signature" of an anthrax particle is similar for example, to the scattered light signature of common dust.

To enhance stand-off biological agent discrimination, other laser based remote sensing techniques have been developed, in particular Laser Induced Fluorescence or LIF. In LIF a short wavelength (typically in the UV or visible spectral range) laser illuminates the particles, the light is absorbed and subsequently re-emitted at a different (longer) wavelength. By detecting the longer wavelength emission one may infer that a biological aerosol is present (since inorganic materials tend not to fluoresce). However, there is frequently little in the fluorescence signature that permits one to distinguish one biological species from another.

Other techniques such as Raman lidar have been applied to chemical concentration mapping and aerosol extinction measurements but are not useful for aerosol discrimination or identification. Differential absorption lidar (DIAL) is another method that permits one to probe spectral absorbing features remotely by tuning a probe laser on and off the absorption line. However, biological species are chemically similar to each other and have spectrally broad absorption features similar to chemicals such as hydrocarbons. This makes it very difficult to spectrally distinguish hazardous bioaerosol from benign bioaerosol and other background atmospheric chemicals. Aerosol depolarization measurements have also been investigated and used to distinguish stratospheric ice from water droplets. However, application of this technique to bioaerosol discrimination has proven to be only weakly effective with depolarization variations due to the type of aerosol being much less pronounced than changes due to the aerosol concentration (see, for example, J. H. Marquardt et al., "*Measurement of bio-aerosols with a polarization-sensitive, coherent Doppler lidar*", 5th Joint Conference on Standoff Detection for Chemical and Biological Defense, Williamsburg, Va., Sep. 24-28, 2001). This prevents pure depolarization measurements from serving as an aerosol discriminator outside of laboratory conditions. Passive methods (see e.g. Theriault et al. "*Passive standoff detection of BG aerosol. Method and field trial results*", Proc. of SPIE pp. 163, vol. 5268, 2004) have also been used but do not lend themselves to a high degree of discrimination between species especially at stand-off ranges.

What is needed is a method that is capable of and discriminating hazardous biological agents to enable suitable action to be taken when a threat species is found. In addition the method should desirably permit detection at stand-off ranges of hundred of meters or even more desirably several kilometers. The technique should also be capable of day or night operation.

SUMMARY OF THE INVENTION

The invention disclosed in the present application meets these conditions, and has been demonstrated to detect and discriminate *bacillus globigii* (BG), an anthrax simulant, against a collection of other particles. The present invention makes use of two or more wavelengths of light in conjunction with polarization measurements to perform detection and discrimination of species of interest. In the simplest form, a laser transmitter generates a plurality of wavelengths in a light beam having a predetermined state of polarization (SOP). Light scattered from the target particles is detected at the multiple wavelengths using polarization sensitive receivers and the degree of change in polarization of the scattered light is determined. The ratio of the depolarization at two or more wavelengths is then calculated and used to discriminate between the various species.

DETAILED DESCRIPTION OF THE PREFERRED EMBODIMENTS

1. Light Depolarization

Figure 1:
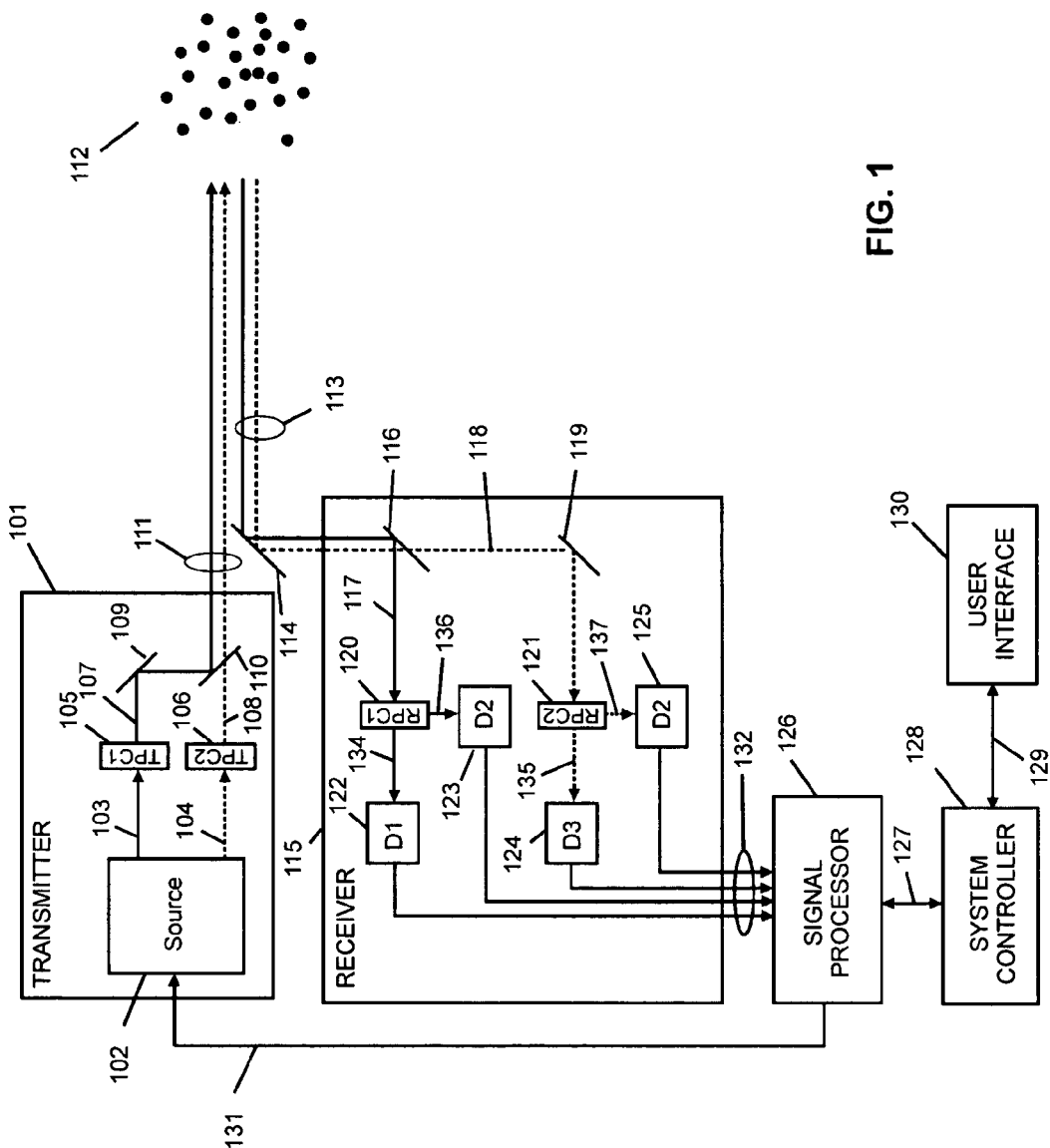
FIG. 1 shows the general architecture of a lidar system of the present invention.

Polarization is the property of light that describes the orientation of the electric field vector perpendicular to the propagation axis of a light beam as discussed, for example, in the text *Optics* by Eugene Hecht, Addison Wesley 2001, hereby incorporated by reference. The photons that make up a light beam have either a right-hand or left-hand circular polarization state, meaning that the polarization vector rotates clockwise or counter-clockwise about the propagation axis. All other polarization states that may describe a light beam result from a linear combination of these states. For example, horizontal (h) and vertical (v) linear states result from equal amounts of right-hand and left-hand light with the proper phase relationships between the circular states. Two polarization states are said to be orthogonal if the product of the polarization vectors is zero, as is the case for the two circular states and the two linear states. It is well known that interaction of photons with materials frequently alters the polarization state such that light prepared in a given polarization state that is backscattered from small particles, may show a different polarization state than was incident. An example of this is the scattering of light from ice particles in Cirrus clouds, as discussed, for example, by Grant in "*Lidar for Atmospheric and Hydrospheric Studies*", in Tunable Laser Applications, F. J. Duarte ed., Marcel Dekker 1995, hereby incorporated by reference. This alteration of a polarization state as a result of an interaction with the material can be used to discriminate different materials. As used herein the word "discriminate" means to broadly classify such as classifying whether a particle is biological in nature as opposed to non-biological material, or to discriminate whether an aerosol is hazardous or benign. Discriminating does not require specific identification of a material. In the most general terms an incident polarization state can be uniquely described by a Stokes vector u and the effect of the material on the polarization can be described by a Mueller matrix M, so that the Stokes vector of the scattered light is described by vector u' according to the relationship u'=M·u. The Mueller matrix itself is dependent on the material, and in the case of small particles it is highly dependent on the microscopic structure of the particles.

"Normalized depolarization" of light can be described by the relationship:

$$N\delta_{i,j} = \frac{P_i}{P_j + P_i} \quad (1)$$

where $P_j$ represents the scattered power measured in the same polarization state as the transmitted beam and $P_i$ represents the scattered power in an orthogonal polarization state. In a case where the scattered light is the same as the incident polarization state $N\delta_{i,j}=1$, whereas when the light has been completely changed into the $j^{th}$ state $N\delta_{i,j}=0$. Complete depolarization, where there are equal amounts of power in the $i^{th}$ and $j^{th}$ states, gives $N\delta_{i,j}=0.5$.

The present invention recognizes that simple depolarization measurements as described by equation 1 are frequently insufficient to discriminate materials. However, relating depolarization measurements carried out at multiple wavelengths does permit such discrimination. This is due to the fact that a simple depolarization measurement provides some information about, for example, the morphological structure of the particles. In contrast, carrying out the measurement at multiple wavelengths allows one to exploit the fact that the Mueller matrix of the material may be altered locally (in wavelength) due to, for example, absorption in the constituent particles. In the disclosed "Wavelength Normalized Depolarization Ratio" technique (WANDER), the ratio of the normalized depolarization at two wavelengths is determined. The 2-wavelength ratio, referred to herein as the "WANDER ratio" ξ, for wavelengths $\lambda_1$, and $\lambda_2$, is calculated as $$\xi_{\lambda1,\lambda2} = \frac{\frac{P_{\lambda_1,i}}{P_{\lambda_1,j}+P_{\lambda_1,i}}}{\frac{P_{\lambda_2,i}}{P_{\lambda_2,j}+P_{\lambda_2,i}}} = \left(\frac{P_{\lambda_1,i}}{P_{\lambda_2,i}}\right) \cdot \frac{P_{\lambda_2,j}+P_{\lambda_2,i}}{P_{\lambda_1,j}+P_{\lambda_1,i}} \quad (2)$$

2. General System Architecture

A general system to carry out the measurements necessary to calculate the WANDER ratio is shown in FIG. 1. The overall architecture of the system is to produce light at two wavelengths in a well-defined polarization state with a transmitter subsystem 101, measure the depolarization at both wavelengths using a receiver subsystem 115 and then calculate the ratio given by equation 2 using a signal processor 126. To accomplish this the system incorporates a source 102 that outputs two light beams 103 and 104 at different wavelengths. Beams 103 and 104 are passed through transmit polarization controllers (TPC) 105 and 106 that ensure that beams 107 and 108 have the desired polarization states. These TPCs may be absent if the beams 103 and 104 already have desired polarization states, for example linear, but generally comprise polarizers and/or optical retarders to produce the desired states. Beams 107 and 108 are next combined using optics 109 and 110 such that the two beams overlap spatially and in propagation angle, effectively forming one beam 111 (for clarity shown in FIG. 1 as two spatially separated lines). Depending upon the measurement scenario it is not strictly necessary to combine the beams into a single overlapping beam, but it is frequently desired to ensure that all wavelength beams interact with the same scattering centers. The combination optics may comprise, as examples, dichroic coatings or diffraction gratings. The combined beam 111 is transmitted to scattering centers 112 where the light interacts with the scatterers to produce scattered light 113 propagating towards the receiver 115. Again light at the two wavelengths is illustrated in FIG. 1 as two separated lines for clarity, but generally the scattered light at the two wavelengths overlaps spatially. The light is directed into the receiver 115 using mirror 114 and is directed to a wavelength separating optic 116. This optic, which may again be a dichroic coated substrate or a diffraction grating, separates the two wavelengths into beam 117 at one wavelength and beam 118 at the other wavelength.

Beam 118 is next redirected using mirror 119 and both beams 117 and 118 are passed through receive polarization controllers (RPC) 120 and 121 before being detected at detectors 122 through 125. The RPCs act as polarization analyzers that transmits the fraction of light present in one predetermined polarization state as beams 134 and 135 for detection at 122 and 124, while reflecting the orthogonal polarization state as beams 136 and 137 for detection at 123 and 125. In a simple case where the desire is to separate the receive beams into linear polarization states the RPCs 120 and 121 may be linear polarizers. In other cases the RPCs may contain a combination of fractional waveplates and polarizers to perform the action of separating the received light into two orthogonal polarization states for detection. In cases where measurements at different polarization states are carried out sequentially the RPCs are set to transmit a first polarization state and then switched to transmit an orthogonal state. In such cases only two detectors are required. In this example the returned light is first separated by wavelength and then by polarization state. Alternatively the light could be first separated by polarization state and then by wavelength.

The light detected by detectors 122-125 is converted into signals 132 that are captured by signal processor 126. In the case of using 4 detectors all four signals are captured by the processor that subsequently calculates the WANDER ratio according to equation 2. In case of using two detectors and changing receive polarization states between detection events measurements are first carried out for one polarization state and data captured, followed by a change in the analyzer settings and collection of data at the orthogonal polarization state. The signal processor 126 then calculates the WANDER ratio from the two data sets.

The processed data is output as a signal 127 to a system controller 128 that normally also outputs a signal 129 to a user interface 130 that may be a display, a data storage device, an alarm, or any other suitable device. System controller 128 normally also carries out additional functions that are practically useful but not essential to the operating principle of the invention. Such functions may include control of the transmit source via a connection 131, communications and/or control of the signal processor via 127, as well as control of the transmit and receive polarization controllers in cases where these are not fixed. In a common situation the system as described would be used in conjunction with a scanning system that permits pointing the transmit beam over an angular range to scan a volume of space in search of specific species of interest. It is also stressed that operational systems frequently do not need all elements shown in FIG. 1. For example, if laser or non-linear frequency converted laser beams are used as the lights source it is common that the light beams are linearly polarized. In cases where illumination with a linearly polarized beam is suitable the TPCs 105/106 would not be required. In such a case the receiver would require only simple polarizers as RPCs in order so detect linear polarization states.

In the context of light sources it is noted that both continuous-wave (CW) and pulsed devices can be used in the invention, provided only that a suitable source is available. Under some circumstances pulsed sources are preferred. One such circumstance is when the interrogated volume of interest is between the source and a reflecting surface, such as the ground. If a CW source is used the receiver may pick up scattered light from the reflecting surface whose magnitude far exceeds the signals from the particles of interest, thereby making the measurements difficult or impossible. A pulsed source having a pulse duration of for example 0.1-1000 ns permits one to time resolve and hence range resolve the scattered signals so that light from the particles arrives back at the receiver before a potentially much bigger signal arrives from the background. A second advantage of pulsed sources is that it is frequently convenient to generate the desired operating frequency by converting light from a fixed frequency laser using an optical parametric oscillator (OPO) or similar device. This is so because many probe wavelengths of interest fall in the mid-infrared part of the spectrum where direct lasers with sufficient wavelength tuning capability are less common. The efficiency with which OPOs operate is dependent upon the peak power of the pump laser source. Using a pump laser with short pulses having high peak power is normally far more efficient than converting a CW pump laser.

3. Demonstration System

Figure 2:
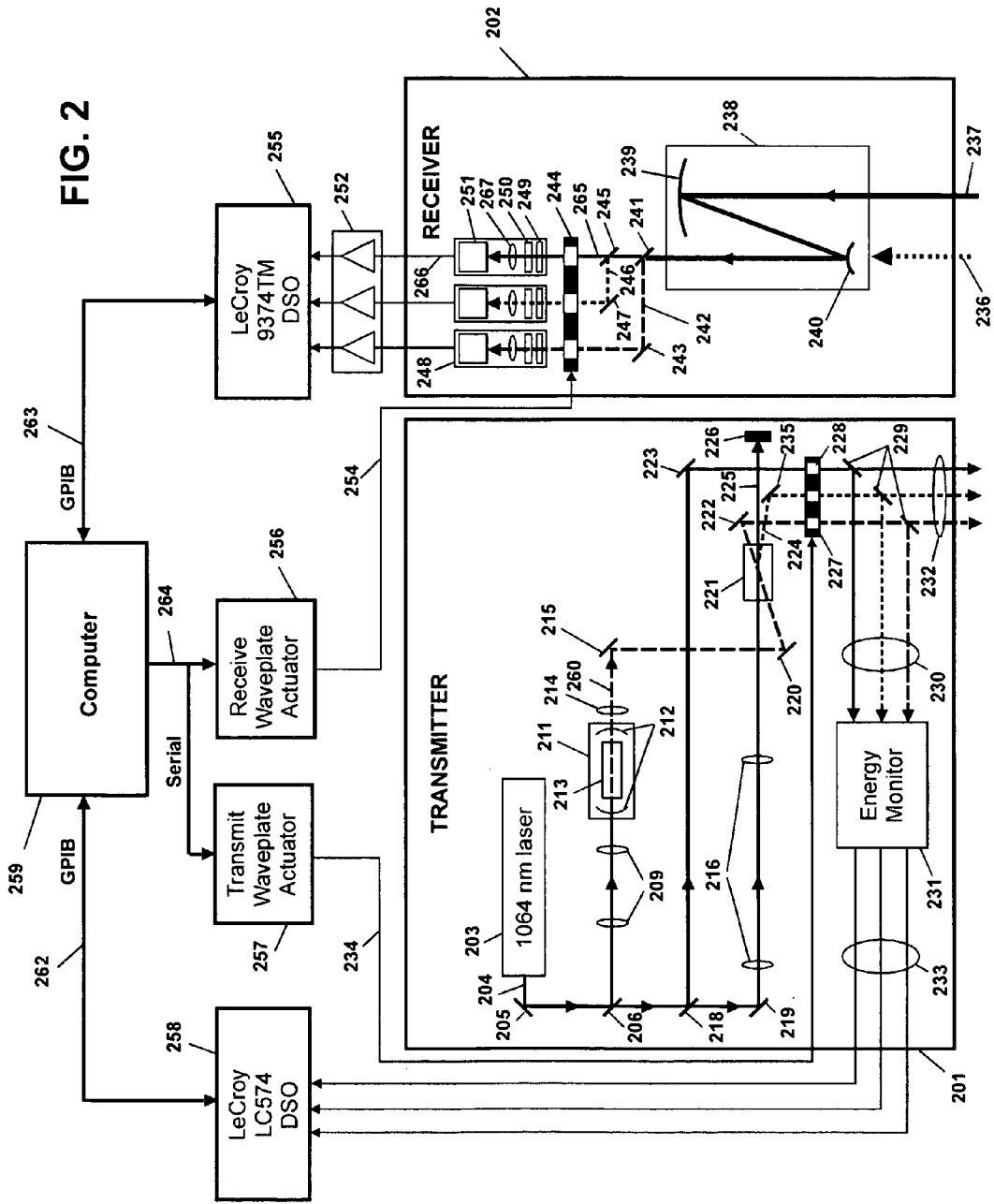
FIG. 2 shows an implementation used to detect and discriminate *bacillus globigii* (BG) from other substances.

The inventors have constructed a system according to the invention and demonstrated its usefulness in discriminating the anthrax stimulant BG (*Bacillus Globigii*) against a wide range of other dispersed samples. Airborne anthrax is a highly deadly biological agent and the capacity of the present invention to remotely distinguish it from background material is a very significant advance in the detection of biochemical warfare agents. The system implemented is illustrated in FIG. 2 and has a high degree of functional similarity with the architecture illustrated in FIG. 1, but operates with three wavelengths instead of two. In the implemented system numeral 201 indicates the transmitter portion of the system and 202 indicates the receiver portion. The transmitter portion incorporates a commercial laser 203 (Spectron Laser model SL484) operating at 1064 nm and producing approximately 150 mJ pulse energies at a pulse repetition frequency (PRF) of 30 Hz with a pulse width of 16 ns. The output beam 204 from laser 203 is directed with mirror 205 to beam splitter 206 where a portion of the beam is transmitted to beam splitter 218. The portion of the beam reflected from beam splitter 218 is directed to mirror 223 which directs it to a waveplate assembly 228 contained in motorized assembly 227.

The portion of laser beam 204 that is reflected from beam splitter 206 is transmitted through lenses 209 that form a telescope for mode matching the beam into OPO assembly 211. The OPO assembly 211 comprises mirrors 212 surrounding $LiNbO_3$ crystal 213. When pumped with the 1064 nm beam part of the 1064 nm energy is converted into a beam 260 at a wavelength of 3389 nm that propagates through lens 214 and is reflected from mirrors 215 and 220 and through optical parametric amplifier (OPA) 221 comprising a crystal of $LiNbO_3$. The third part of 1064 nm beam 204 that is transmitted through beam splitter 218 is reflected from mirror 219 before passing through a mode matching telescope comprising lenses 216. This beam pumps OPA 221. In the process unconverted 1064 nm light 225 is dumped at beam dump 226. The amplification action increases the energy of beam 260, which continues through the crystal and is reflected from mirror 222 and is directed to a second waveplate assembly in motorized assembly 227. The OPA also creates a signal beam 224 at a wavelength of 1551 nm that is reflected from mirror 235 and propagates to a third waveplate assembly in motorized assembly 227. Motorized assembly is controlled by a transmit waveplate actuator 257 via electrical connection 234. The motorized assembly 227 permits rotation of waveplates 228 to cause the polarization state of the three incident laser beams to be altered under computer control. The laser beams 232 emerging from assembly 227 form a set of three transmit laser beams that illuminate a target (not shown) at a suitable distance away from the transmitter. In order to account for variations in power among the three beams sampling beam splitters 229 pick off a small amount of the laser energy and directs the sampled beams 230 to an energy monitor 231 that contains detectors that in turn transmit signals 233 to a digital oscilloscope 258 (LeCroy model LC574). In the demonstrations it was found not to be necessary to use beam combination means to ensure that all beams overlap spatially at the transmitter.

Light 237 scattered from the target particles enters a receiver telescope 238 comprising a large primary mirror 239 and a smaller secondary mirror 240 which causes the received beam to be demagnified and matched in size to the subsequent detectors. At this stage scattered light at all wavelengths overlap in space and time. The overlapped beam is incident on a dichroic optic 241 that reflects the 3389 nm light 242 and directs it to mirror 243, which in turn redirects the light towards receive waveplate assembly 244. The 1064 nm and 1551 nm light transmitted through dichroic 241 continues propagating to a second dichroic optic 245 that reflects the light at 1551 nm as beam 246, which reflects from mirror 247 and is also directed towards receive waveplate assembly 244. The 1064 nm light transmits through both dichroics 241 and 245 and is then incident on waveplate assembly 244. The waveplate assembly is similar in construction to transmit waveplate assembly 227 in that it contains three sets of waveplates whose angular orientation can be controlled remotely by receive waveplate actuator 256 via connection 254 to select a desired polarization state for subsequent detection. The three beams are transmitted through the corresponding waveplates in assembly 244. Each beam then enters a separate receiver 248 that contains four elements. The first element is a polarizer 249 that in conjunction with the corresponding waveplate in assembly 244 permits selection of a polarization state for detection. The second element is a bandpass filter 250 that passes a narrow wavelength range near the corresponding scattered light. This has the effect of reducing noise by rejecting stray background light. The third element is a lens 267 that focuses the received light onto the fourth element, the detector 251 that converts the optical signal to an electrical signal 266. For the demonstration system the detectors used for 1064 and 1551 nm were conventional InGaAs PIN detectors (Hamamatsu model G8376-05), while the 3389 nm detector was a Denber effect InAs device (Vigo, Poland).

The three electrical outputs from the detectors are next passed through a set of amplifiers 252 where the electrical signal is boosted before being sampled using a digital oscilloscope 255 (LeCroy model 9374TM). The signals from the two oscilloscopes 258 and 255 communicate with a personal computer 259 via GPIB and custom written Labview software. This enables the computer to extract transmitted and received energy at all three wavelengths. The computer 259 further outputs serial data 264 to waveplate actuators 257 and 256. This flexibility enables the system to independently vary the transmit and receive polarization states and collect data for a large set of polarization state settings in a short time.

The telescope 238 is primary used for collection of data from relatively distant ranges where the large collection aperture (2" diameter) of primary mirror 239 is beneficial. In the experiments carried out at short ranges the telescope was not necessary and was removed. As a result the received light entered the receiver system along direction 236. A further note is that the transmitter and receiver portions of the system were aligned relative to one another such that the receiver looked at the region of space illuminated by the transmit beam.

Figure 3:
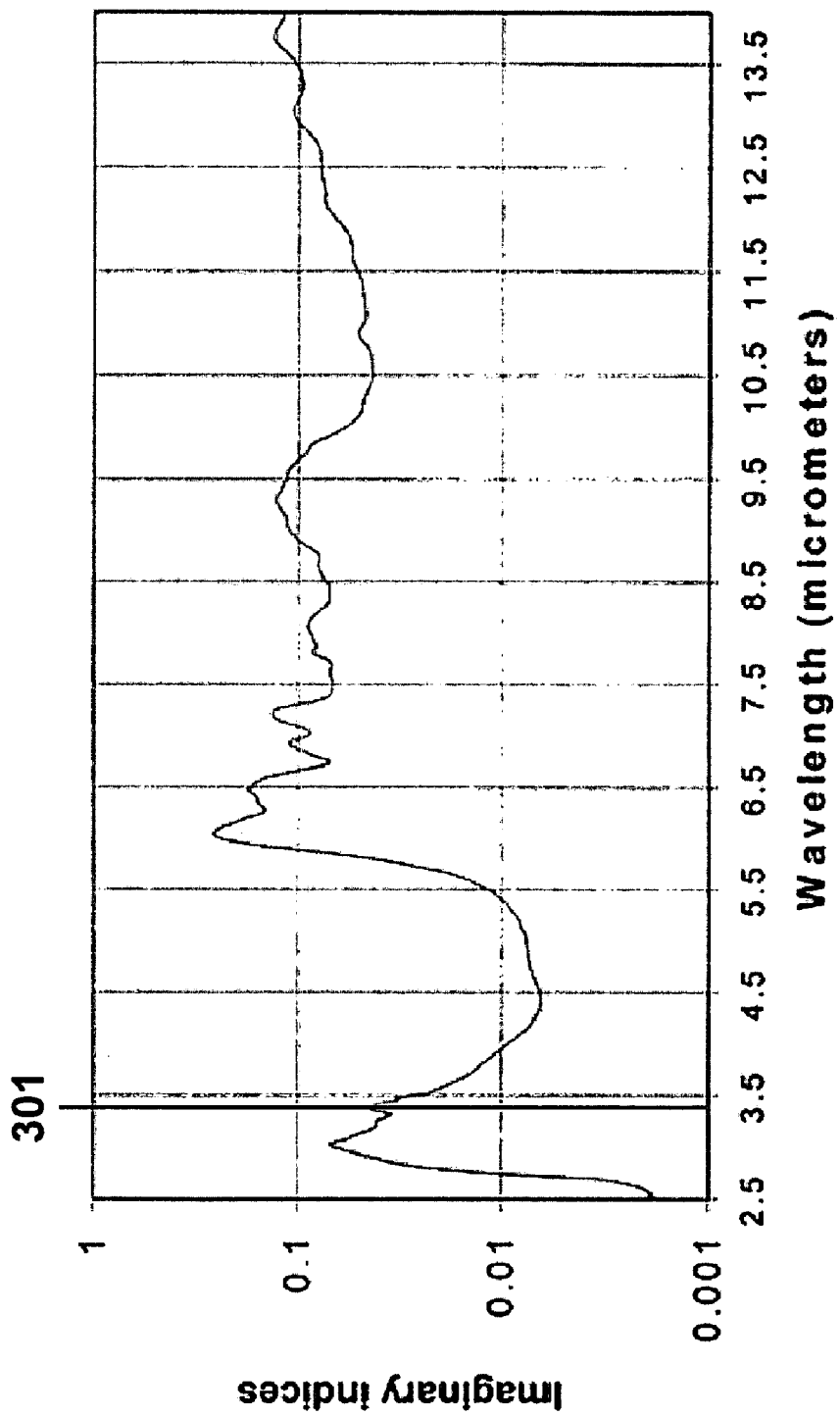
FIG. 3 is a plot of the absorption spectrum of BG in the vicinity of the 3.4 micron wavelength used with the demonstration system.

The system as described was used to collect light scatter data from a number of different substances, among them the anthrax stimulant BG. The substances were released in a controlled environmental chamber. All samples were released in dispersed particle form with individual particles having typical sizes in the micrometer range. Following data collection the PC was used to calculate the depolarization ratio. Since three wavelengths were available for a given set of polarization states three depolarization ratios could be calculated, namely the ratios at 1064/1551, 1551/3389, and 1064/3389. The 1551 nm wavelength was used because it was available "for free", being the byproduct of the 1064 nm conversion to 3389 nm. The 3389 nm wavelength was chosen specifically because it falls in a region of good atmospheric transmission as well as coinciding with an absorption peak in the spectrum of BG. The imaginary part of the complex refractive index (proportional to the absorption coefficient) spectrum of BG (as published by K. P. Gurton, D. Ligon, and R. Kvavilashvili, "*Measured infrared spectral extinction for aerosolized Bacillus subtilis var. niger endospores from 3 to 13 μm,*" Applied Optics, 40(25), 2001, hereby incorporated by reference) is shown in FIG. 3 with line 301 indicating the wavelength at which the measurements were carried out.

While the invention is not limited to a specific mechanism for depolarization it is known that the efficiency of light scattering from particles is dependent on the wavelength of incident light and the size of the particle. The light wavelength and the particle size may also impact the ability of light to penetrate a particle. Furthermore, it is believed that the presence of strong absorption in BG at 3389 nm will suppress the depolarization that is observed relative to less strongly absorbed wavelengths. As a result one would anticipate that aerosols will show a WANDER ratio dependence on the selection of wavelengths.

Figure 4:
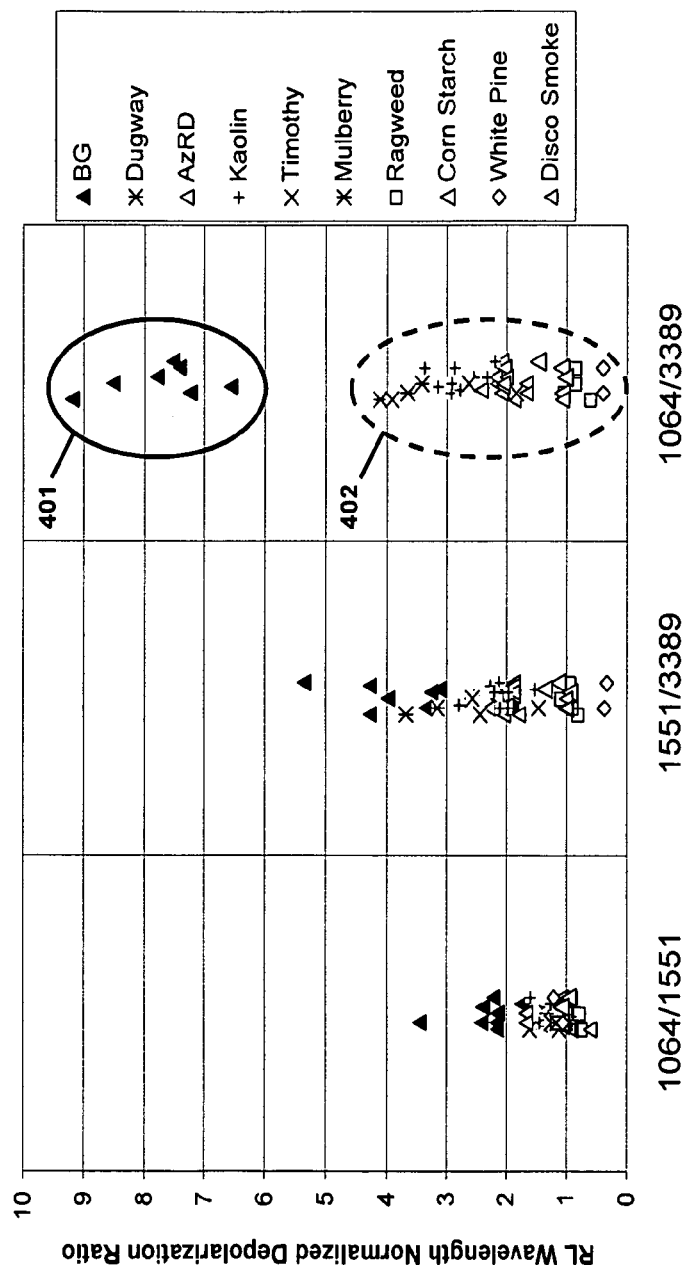
FIG. 4 is a plot of data collected and processed by the demonstration system.

FIG. 4 illustrates a sample result of the measurements in the case where right circular polarized light was transmitted and left circular scattered light contributions were detected. Strong changes in depolarization give a high depolarization ratio whereas weak depolarization changes give a low depolarization ratio in these measurements. The leftmost column shows a WANDER calculation for the 1064/1551 nm case. BG corresponds to the filled triangles. Multiple sets of data were collected and measured resulting in some data scatter for each species. The other data was calculated for the following substances: Dugway=dirt from Dugway Proving Ground, AzRD=Arizona road dust, Kaolin, Timothy, Mulberry, Ragweed, Corn starch, White Pine, and disco smoke released sequentially into the test chamber. For the 1064/1551 nm data there is little significant difference between the materials. The center column shows 1551/3389 nm WANDER data and there is a tendency for the BG data points to separate. The third column case of 1064/3389 nm data clearly shows the BG data points 302 separated from all other materials 301. The large ratio of depolarization at the 1064 and 3389 nm wavelengths is consistent with the notion that depolarization is strongly suppressed at the longer wavelength for BG. This is a strong indication that the invention is capable of discriminating between the anthrax simulant and other substances including dust and pollens that may be present as naturally occurring background. As noted it is believed that the mechanism for this clear separation of data is the presence of absorption in BG at 3389 nm, but the actual mechanism is not essential to operation of the invention. What is important is that operation of a system of the present design can exploit variations in materials to extract data that permits discrimination between the materials.

4. Alternative Embodiments

Numerous alternative and beneficial embodiments of the invention are possible. One alternative embodiment uses a tunable or multi-wavelength source to produce probe light over a predetermined spectral range to collect data at a multiplicity of wavelengths. When coupled with a database of calibrated depolarization ratio measurements this can be used to match measured data with the database to identify one or more species indicated by the data. It is also likely that further measurements indicate that the depolarization ratio shows a spectral signature similar to other signatures like absorption spectra, in which case correlation analysis over a wide spectral range may be used to identify multiple species even if they are present simultaneously. The construction of a tunable system of this nature is not dependent on a particular type of light source, but one exemplary type is an electrically tunable Cr:ZnSe solid-state laser pumping an OPO as described by A. Zakel et al. in "*High-brightness rapidly-tunable Cr:ZnSe lasers*", 20$^{th}$ Anniversary Meeting Advanced Solid-State Photonics, Feb. 6-9, 2005, Vienna. Rapid electrical tuning of a Q-switched Cr:ZnSe laser has been demonstrated over a spectral range of 2.1-2.8 μm and use of this laser to pump an OPO (for example $ZnGeP_2$ or CdSe) can provide a pulsed source covering the mid- to long-wave infrared spectrum from approximately 2-14 μm.

From an operational and low cost standpoint is may be beneficial to construct simple systems that use only two wavelengths and use fixed transmit and receive polarization controllers, for example transmitting one linear polarization state and receiving two linear polarization states for the WANDER ratio calculations. Polarization states useful in a particular application are determined through calibration experiments prior to construction of the system. However a more complicated system that transmits and collects four polarization states and calculates the entire Mueller matrix of the material may provide greater discrimination ability. With four polarization states measured for each of two wavelengths up to 16 ratios can be calculated. Selecting an optimal set of depolarization ratios may result in greater discrimination than a single depolarization ratio.

Although the system has been described primarily in terms of usefulness to making measurement with scalability to long ranges, it is equally clear that the method is also useful for short-range measurements, for example in scanning mail and parcels at sorting stations for the presence of undesired airborne materials. In such short-range cases it is generally not required that the light source produce highly energetic pulses. To reduce complexity and cost diode-lasers, LEDs, and filtered broadband emitters may be advantageously utilized.

Yet one more alternative embodiment would use a wavelength switchable source to output several wavelengths and/or polarizations for sequential measurements. Implementing such a system may enable the use of as few as a single broadband detection channel provided that the receiver incorporates means as discussed to switch between receive polarization states. A system using two detection channels could be constructed to receive two polarization states simultaneously and wavelength switching used to collect data at the plurality of wavelengths.

The demonstrated system can be improved upon in a number of areas. Use of a telescope as noted with reference to FIG. 2 will significantly extend the range at which detection can take place. Optimization of detectors to minimize noise would also be beneficial, for example utilizing photon-counting detectors. One possibility is the use of HgCdTe APD detectors that have the potential for very low noise detection over a very wide spectral range from <1 μm to >10 μm. Scaling of the results obtained indicate that systems can be built that permit operation at stand-off ranges exceeding 1 km. For operational use a scanning system is also beneficial to enable coverage of a large volume in space. Such a system can also easily be used in conjunction with geolocation (e.g. GPS) and direction sensors to identify the absolute or relative location of detected species. When a pulsed light source is used the time delay between transmission and reception of the scattered light can be used to determine range to the scatterers, which, in conjunction with the aforementioned GPS and/or direction sensors can be used to determine the 3 dimensional coordinates of the scatterers. A system used in this manner can easily report the presence and/or location of species to emergency response teams or other designated responders.

The objective of the demonstration system discussed with reference to FIG. 2 was to demonstrate discrimination of BG against other materials, but a system using the described method can be used to detect a wider range of materials provided that the materials are characterized spectrally with respect to depolarization properties.

Throughout this disclosure the term "light" has been used to describe the radiation emitted and detected. It is noted that this term should be interpreted in broad terms, covering the entire electromagnetic spectral range, rather than being used to denote a specific range of radiation frequencies.

A further alternative use of the system is in conjunction with a second lidar system, where the second system is capable of detecting the presence of aerosols or other emission plumes over a large area or volume through rapid scanning, and the disclosed invention is subsequently utilized to probe the detected area/volume for the presence of specific chemical or biological agents of interest. This arrangement may be particularly useful if the area/volume search rate of the second system is greater then that of the invention.

The benefits of the present invention enable a number of applications that include, but are not limited to: Remote detection and characterization of aerosols, mapping distributions of dispersed airborne material, and early warning of unintentional or intentional release of biological agents. Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

We claim:

1. A remote detection system comprising:
   a transmitter configured to transmit electromagnetic energy at a first wavelength and a second wavelength, wherein the transmitted electromagnetic energy has a selected polarization state;
   a polarization sensitive receiver positioned to receive scattered electromagnetic energy that has been scattered by materials illuminated by the transmitter, wherein the receiver generates signals indicating power of the scattered electromagnetic energy at selected polarization states; and
   a signal processor coupled to the receiver signals, wherein the signal processor is configured to compute depolarization at the first wavelength, depolarization at the second wavelength, and a ratio of the depolarization at the first and second wavelengths.

2. The remote detection system of claim 1 wherein the transmitter is configurable to alter the selected polarization state of the transmitted electromagnetic energy.

3. The remote detection system of claim 1 wherein the transmitter is configurable to alter the wavelength of the transmitted electromagnetic energy.

4. The remote detection system of claim 1 wherein the receiver comprises two detectors where each of the detectors measures a polarization state simultaneously.

5. The remote detection system of claim 1 wherein the receiver comprises a single detector shared by each of the first and second wavelengths.

6. The remote detection system of claim 1 wherein the transmitter transmits the first and second wavelengths simultaneously.

7. The remote detection system of claim 6 wherein the signal processor computes depolarization at the first wavelength and depolarization at the second wavelength substantially simultaneously.

8. The remote detection system of claim 1 wherein the transmitter transmits the first and second wavelengths at separate times.

9. The remote detection system of claim 1 further comprising a device coupled to monitor the power of the transmitted electromagnetic energy.

10. The remote detection system of claim 1 wherein the transmitted electromagnetic energy is pulsed.

11. The remote detection system of claim 1 wherein the transmitted electromagnetic energy is continuous wave.

12. The remote detection system of claim 1 wherein the transmitter comprises a device selected from the group consisting of: lasers, non-linear optical sources, light emitting diodes, and filtered broadband sources.

13. The remote detection system of claim 1 further comprising a telescope optically coupled to the receiver and positioned to gather the scattered electromagnetic energy.

14. The remote detection system of claim 1 further comprising a spatial scanning system coupled to the transmitter.

15. The remote detection system of claim 1 further comprising a geolocating component operable to locate materials that scatter the transmitted electromagnetic energy in two or three spatial dimensions.

16. The remote detection system of claim 1 further comprising:
one or more stored signatures, wherein each signature corresponds to a depolarization ratio of a material of interest;
means for comparing a computed depolarization ratio with the stored signatures to determine a match; and
a notification system coupled to the means for comparing to create an automatic notification in response to the match determination.

17. The system of claim 1 wherein the transmitter is configured to generate electromagnetic energy at three or more wavelengths.

18. The method of claim 1 further comprising:
using the depolarization ratio at the first wavelength and/or the depolarization ratio at the second wavelength to determine whether the materials illuminated by the transmitter are hazardous.

19. A method for remote detection comprising:
transmitting electromagnetic energy at a first wavelength and a first selected polarization state;
transmitting electromagnetic energy at second wavelength and a second selected polarization state;
detecting scattered electromagnetic energy that has been scattered by materials illuminated by the transmitter;
generating signals indicating power of the scattered electromagnetic energy at selected polarization states;
computing depolarization at the first wavelength, computing depolarization at the second wavelength, and computing a ratio of the depolarization at the first and second wavelengths; and
outputting information corresponding to the ratio of the depolarization at the first and second wavelengths to one or more of: a storage device, a display and an alarm.

20. The method of claim 19 further comprising:
altering the selected polarization state of the transmitted electromagnetic energy.

21. The method of claim 19 further comprising:
altering the wavelength of the transmitted electromagnetic energy during the act of transmitting.

22. The method of claim 19 wherein the act of generating signals indicating power of the scattered electromagnetic energy at selected polarization states for both the first and second wavelengths is performed substantially simultaneously.

23. The method of claim 19 wherein the act of detecting comprises using a single detector to detect electromagnetic energy scattered at both the first and second wavelengths.

24. The method of claim 19 wherein the acts of transmitting electromagnetic energy at the first wavelength and transmitting electromagnetic energy at the second wavelength are performed substantially simultaneously.

25. The method of claim 19 wherein the acts of transmitting electromagnetic energy at the first wavelength and the act of transmitting electromagnetic energy at the second wavelength are performed at separate times.

26. The method of claim 19 wherein the acts of computing depolarization at the first wavelength and computing the depolarization at the second wavelength apply an equation of the form:

$$N\delta_{i,j} = \frac{P_i}{P_j + P_i}$$

where $P_j$ represents scattered power measured in the same polarization state as the transmitted beam and $P_i$ represents scattered power in an orthogonal polarization state.

27. The method of claim 26 wherein the act of computing the ratio comprises applying an equation of the form:

$$\xi_{\lambda_1,\lambda_2} = \frac{\frac{P_{\lambda_1,i}}{P_{\lambda_1,j} + P_{\lambda_1,i}}}{\frac{P_{\lambda_2,i}}{P_{\lambda_2,j} + P_{\lambda_2,i}}} = \left(\frac{P_{\lambda_1,i}}{P_{\lambda_2,i}}\right) \cdot \frac{P_{\lambda_2,j} + P_{\lambda_2,i}}{P_{\lambda_1,j} + P_{\lambda_1,i}}$$

where $P_{\lambda_1,j}$ represents scattered power measured at the first wavelength in the same polarization state as the transmitted beam and $P_{\lambda_1,i}$ represents scattered power at the first wavelength in an orthogonal polarization state; and where $P_{\lambda_2,j}$ represents scattered power measured at the second wavelength in the same polarization state as the transmitted beam and $P_{\lambda_2,i}$ represents scattered power at the second wavelength in an orthogonal polarization state.

28. The method of claim 19 further comprising: using at least one depolarization ratio to determine whether the materials illuminated by the transmitter are hazardous.

29. The method of claim 19 further comprising:
using at least one depolarization ratio to discriminate materials illuminated by the transmitter.

30. A method for remote detection comprising:
transmitting electromagnetic energy at a first wavelength and having a polarization state given by a first Stokes vector;

transmitting electromagnetic energy at a second wavelength and having a polarization state given by a second Stokes vector;
detecting scattered electromagnetic energy that has been scattered by materials illuminated by the transmitter;
computing a first Mueller matrix from the scattered electromagnetic energy at the first wavelength;
computing a second Mueller matrix from the scattered electromagnetic energy at the second wavelength;
computing at least one depolarization ratio from a component of the first Mueller matrix and a component of the second Mueller matrix; and
outputting information corresponding to the at least one depolarization ratio to one or more of: a storage device, a display and an alarm.

31. The method of claim 30 further comprising:
using at least one depolarization ratio to determine whether the materials illuminated by the transmitter are hazardous.

32. The method of claim 30 further comprising:
using at least one depolarization ratio to discriminate materials illuminated by the transmitter.

* * * * *